United States Patent [19]

Schildknecht et al.

[11] 4,417,676
[45] Nov. 29, 1983

[54] METHOD AND APPARATUS FOR PARTITIONING AND/OR SHAPING A FIBROUS BATT

[75] Inventors: Othmar Schildknecht; Eduardo Cassoli, both of São José dos Campos, Brazil

[73] Assignee: Johnson & Johnson Baby Products Company, New Brunswick, N.J.

[21] Appl. No.: 233,421

[22] Filed: Feb. 11, 1981

[51] Int. Cl.³ .............................................. B26F 3/02
[52] U.S. Cl. ...................................... 225/4; 225/100; 225/101
[58] Field of Search ...................... 225/101, 100, 1, 3, 225/4, 106; 83/117

[56] References Cited

U.S. PATENT DOCUMENTS

| 868,856 | 10/1907 | Firm | 83/117 X |
|---|---|---|---|
| 2,336,957 | 12/1943 | Pierce | 83/150 |
| 2,492,497 | 12/1949 | Oakley et al. | 225/98 |
| 3,794,228 | 2/1974 | Colwill et al. | 225/101 X |
| 3,957,186 | 5/1976 | Babcock | 225/101 X |
| 4,279,369 | 7/1981 | Passafiume | 225/106 X |

FOREIGN PATENT DOCUMENTS 1252050 10/1967 Fed. Rep. of Germany ...... 225/101

Primary Examiner—Frank T. Yost
Attorney, Agent, or Firm—Martha A. Michaels

[57] ABSTRACT

The invention relates to a method and apparatus for partitioning and/or shaping a batt by gripping the batt with resilient means or, alternatively, with resilient means and non-resilient means, and by stressing or severing the batt without the formation of compaction areas on the parted edges of the batt.

1 Claim, 7 Drawing Figures

METHOD AND APPARATUS FOR PARTITIONING AND/OR SHAPING A FIBROUS BATT

The present invention refers to a method and apparatus for partitioning a fibrous batt as discrete individual pieces or panels, such as the absorbent fibrous pulp layers of disposable diapers or sanitary napkins.

Many absorbent products, such as disposable diapers, sanitary napkins, and the like, include an absorbent panel. The absorbent panel is formed of loosely compacted short fibers, such as wood pulp fibers or cotton linters. The panel is produced by taking a source of short fibers such as a pulp board and grinding the board and individualizing the fibers therein using a grinding mill. The individualized fibers are collected on a screen or other permeable means in the form of a layer or batt of loosely associated short fibers. The batt is usually lightly compacted to provide some integrity.

In some absorbent products, a panel of a specific size may be desired while in other absorbent products a panel of a specific size and shape may be desired. In the past, it has been the usual practice to sever sections from an absorbent batt by cutting the batt, as with a knife or scissors. Due to the loose structure of the fibers in such batts, this type of severance often results in permanent compression of the fibers at the severance line. As a result of this compression, the density of the fibers in this region is greatly increased and, consequently, the wickability or preferential absorptivity along the line of permanent compression is greatly increased. This result may be most disadvantageous in the formation of a diaper panel since urine will migrate along a line of densification that comes into contact with it. If this densification line occurs at an edge, as where the panel section has been cut with a knife edge, there is a strong tendency for any liquid coming into contact with the line to be drawn into and concentrated at the line, resulting in premature leakage of urine from the diaper structure. Furthermore, the above method of cutting the batt results in harshness of the batt at the compressed line.

Since the structure of absorbent batts is loose, these batts may be quite easily torn when stressed. Moreover, if the tearing can be done without compressing the fibers of the batt, no densification lines will be created at the edge. U.S. Pat. Nos. 3,895,751 and 3,957,186 disclose devices which tear a batt to form panels without creating densification at the tear line. The first-mentioned patent discloses an apparatus for tearing an intermittently fed batt wherein a pair of juxtaposed opposing jaws operate transversely on a batt to form panels. Each pair of jaws consists of a first jaw and a second biased hinged jaw, so that after the jaws grip the batt, the first jaw holds the batt and the second jaw is displaced from its juxtaposed position, thus tearing the batt transversely. The apparatus of the second patent consists of two opposed, rotatable pairs of batt-engaging cylinders comprising a trailing jaw member and a juxtaposed leading jaw member. The cylinders are simultaneously rotating in opposite directions. As the batt is engaged by the jaws, a displacing means, such as a cam, displaces one cylinder segment of each pair of cylinder segments relative to the other cylinder segments so that the batt is torn. In the instance of each patent there are pivotal means involving displacing jaws so that operational techniques require extra care in cleaning and maintenance and pivoting parts are easily worn.

Another technique for forming individual panels of loose fibers, which may be rectangular in shape or in other desired shapes, without forming the harsh compressed lines produced by cutting the batt is disclosed in U.S. Pat. No. 3,973,291 assigned to Scott Paper Co. In this patent, the panels are formed individually by air laying the fibers within a pattern of the desired size and shape. As described in the aforementioned patent, the machinery required to produce such individually air laid panels and convey such panels is quite large and cumbersome and relatively complex in its moving parts and operation.

Also in U.S. Pat. No. 4,216,687, there is disclosed an apparatus which utilizes air jets to shape and partition a loose batt of fibers into individual shaped panels. While the machine disclosed in the abovementioned patent application is relatively simple in construction and operation, it does require means for generating an air supply and maintaining the air clean which is an added cost in the manufacture of the desired absorbent product.

In a further example, German Pat. No. 1,252,050 to Hesser, a device is shown for separating cardboard sections defined by lines of weakening from a continuous strip of cardboard. The section to be severed from the strip is held between a rubber bar and an underlying roller while the rest of the continuous strip is moved rearwardly by the action of a single, slideably-mounted segment of the underlying roller. In contradistinction thereto, the present invention provides a simple and economical method and apparatus for partitioning a continuously moving batt which is fed between a pair of rolls rotating in opposite directions. The rolls have engaging resilient members such that the batt is partitioned in a manner to provide clean lines with no densification of the batt material.

The present apparatus for partitioning a batt of loosely compacted short fibers into individual panels of short fibers comprises a pair of rolls disposed adjacent each other with axes parallel. The rolls are rotatable in opposite directions but at the same peripheral linear speed. The rolls each have, on exactly-defined positions of their surfaces, two resilient means projecting beyond the surfaces of the rolls, parallel the axes of the rolls, in cases where it is desired to partition the fibrous batt into individual panels, as the simplest embodiment of the invention. In U.S. Pat. No. 4,279,369, the rolls each have at least one jaw member affixed to the roll and extending along the surface of the roll about a portion of the periphery of the roll. When the apparatus is to partition the batt into individual panels, the jaw member is disposed along the surface of the roll parallel to the roll axis, a distance at least equal to the width of the batt being partitioned. When the apparatus is to be used to shape a batt, the jaw member is disposed along the surface of the roll about a portion of the periphery of the roll in the shape or pattern which it is desired to form in the batt. In certain embodiments of the present invention, the rolls may each have at least one jaw member to partition the batt and at least one jaw member to shape the batt.

Each jaw member has a non-resilient means and a resilient means disposed adjacent each other. The non-resilient means is constructed so that the furthest tip of the means projects outwardly from the surface of the roll, in the cases of partition of the pulp batt, or may be constructed so as to consist of an arrangement of matching projections and recesses on the two rolls, in the case of shaping of the pulp batts. The resilient means may project outwardly from the surface of the roll until a little less than the extent of the projection of the non-resilient means and extends along the surface of the roll adjacent the non-resilient means. The apparatus includes a means for rotating the rolls in opposite directions so that the resilient means in the first embodiment grip the batt and, in other embodiments, the jaw members grip the batt such that the non-resilient means of a roll is directly opposed to the resilient means which rotates in opposite direction of the other roll.

The present invention includes a method for partitioning a continuous batt of loosely compacted short fibers into a plurality of discrete panels of fibers. The method includes conveying a batt of loosely compacted short fibers in a direction, gripping the batt transversely between the two first resilient means of the first and second rolls, respectively, reducing the forward displacement speed of the batt by the elastic resistance action of the two first resilient means in penetrating the gap between the two rolls, while at the same time displacing the batt forwardly from the point of greatest proximity of the two rolls at a speed increased by elastic action caused by the sudden projection forward of the two second resilient means of the first and second rolls, respectively, holding the batt before the gap of the rolls and its momentary acceleration after the gap of the rolls being sufficient to partition the batt, gripping by the resilient means, thus assuring the absence of compression lines on the parted edges of the batt.

Further, U.S. Pat. No. 4,279,369 includes a method for partitioning and/or shaping a continuous batt of loosely compacted short fibers into a plurality of individual shaped panels of the fibers. The method includes conveying a batt of loosely compacted short fibers in a direction and gripping the batt along a first path with a resilient means engaging a first surface of the batt and an non-resilient means engaging the second surface of the batt. Substantially immediately thereafter, the batt is gripped along a second path adjacent the first transverse line, with a non-resilient means engaging the first surface of the batt and a resilient means engaging the second surface of the batt. Thereafter, the first and second paths or gripping lines are displaced with respect to each other from the plane of the batt and on opposite sides of the plane. Thus the batt is ruptured. The batt is then released to separate the panel from the remainder of the batt.

A feature of the invention is that the panels are partitioned from a continuously moving absorbent batt without compression of the fibers at the severance lines. In addition, the speed of partitioning the absorbent batt is very high and has been shown to reach about 750 feet per minute. The mechanism of the apparatus of the present invention is quite simple. As a result, it is inexpensive to produce, and easy to operate and maintain. Furthermore, there is little, if any, wear of the parts.

Other advantages of the invention will become evident from the following detailed description and drawings.

Figure 1:
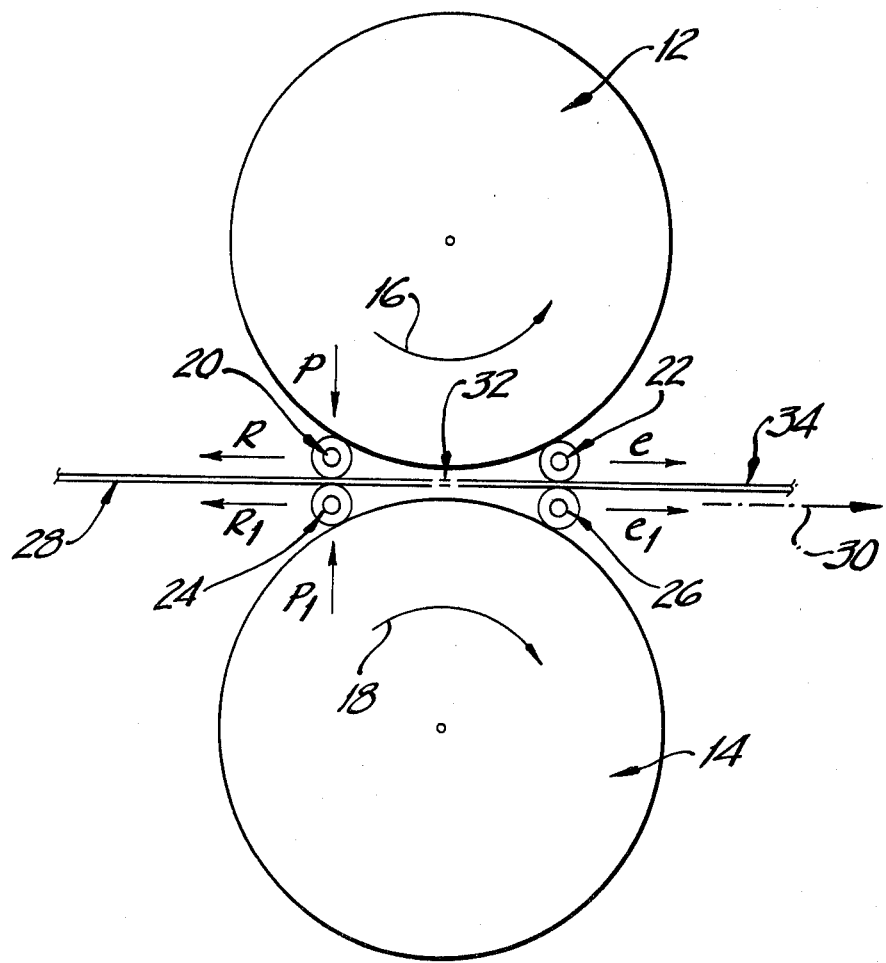
FIG. 1 is a schematic cross-sectional view of an apparatus embodying the present invention.
Figure 2:
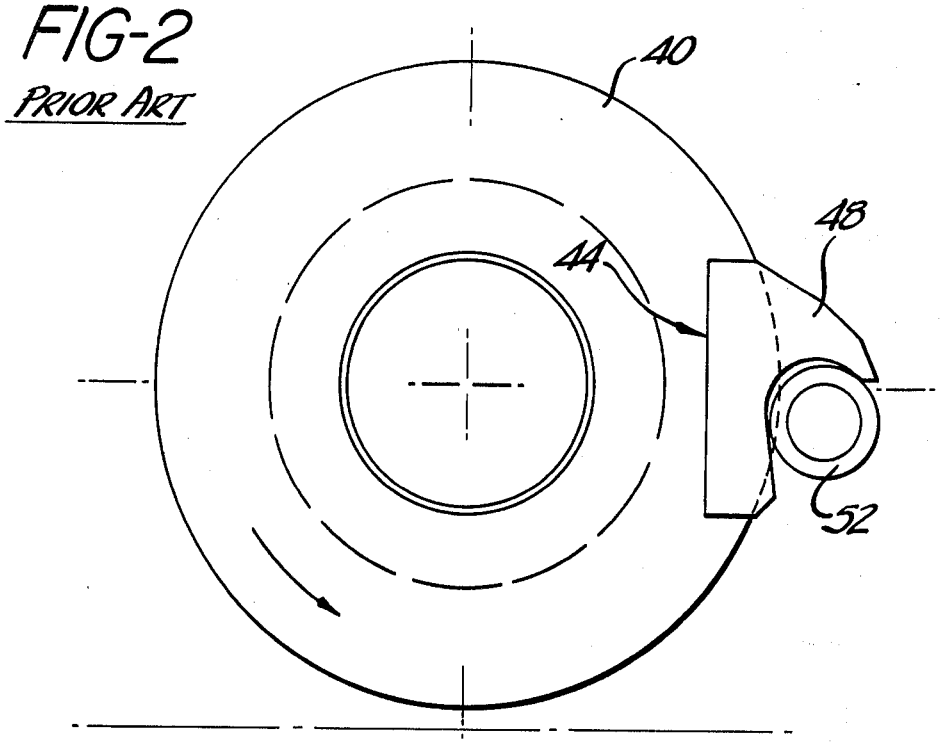
FIG. 2 is a schematic cross-sectional view of a prior art apparatus for the partitioning of panels.

Referring to the drawings, in FIG. 1 there is shown the absorbent batt partitioning apparatus of the present invention. In the apparatus, a pair of rolls 12 and 14 are mounted on a frame (not shown). The rolls are mounted adjacent one another with their axes parallel. The upper roll 12 rotates in the direction shown by the arrow 16, and the lower roll 14 rotates in the opposite direction, indicated by the arrow 18.

The rolls 12 and 14 are provided respectively with resilient means 20, 22 and 24, 26. The resilient means 20, 22, 24 and 26 are, in the embodiment shown here, tubular elements made of a resilient elastomeric material such as, for example, latex, held on the surface of a roll by any conventional means—for example, an adequate adhesive bond—and extend transversely on the rolls, parallel to the axes of the rolls, at predetermined distances in accordance with the length of the individual panels which are to be partitioned from the continuous batt. For a better adhesive contact with the surface of the rolls, small grooves (not shown) may be cut on the surfaces of the rolls 12 and 14 for receiving resilient means 20, 22, 24 and 26.

When rotating, the resilient means 22 and 26 and the resilient means 20 and 24 cooperate to engage simultaneously, each pair 22 and 26; and 20 and 24, the upper and lower surface of a loosely-compacted short fiber batt 28, which is caused to advance in the direction shown by the arrow 30.

The gap between rolls 12 and 14 is sufficient for the passage therethrough, under compression, of the means 20, 22, 24 and 26, with the fibrous batt 28 grasped between them. The speed of advance of the batt 28 is constant.

The severance of batt 28 is made in the following way: the compression to which resilient means 20 and 24 are subjected, the latter having between them the fibrous batt 28, when taken to the gap, or region of greatest proximity of the surfaces of rolls 12 and 14, which compression is indicated by arrows and, generates on the part of resilient means 20 and 24 an elastic reaction against entering the gap, which elastic reaction is indicated by arrows R and R1. Such momentary reaction or resistance causes a delay in the advance of the continuous fibrous batt 28.

Simultaneously, the resilient means 22 and 26, having between them the fibrous batt 28, reach a point where the compression on them is released, which compression is exerted when passing the region of greatest proximity of the surfaces of the two rolls. Such release of resilient or elastic force, indicated by arrows p and $p_1$, causes the fibrous batt 28 to advance relative to its displacement speed in the direction of arrow 30. The combination of the reaction R and R1 towards the delay, with the release p and $p_1$ towards the advance of batt 28, exerts on the latter a tensile force sufficient to sever it at the point indicated by reference number 32, thus partitioning an individual panel 34 in front of the rolls 12 and 14. The compression force p and $p_1$ is not sufficient for the formation of compression lines on the edge of pulp batt thus separated.

Such method and apparatus, whose operation is based on the resiliency of the means 20, 22, 24 and 26, produce excellent results in partitioning fibrous batts 28 of a smaller thickness. For batts of greater thicknesses, the prior art apparatus shown in FIGS. 2, 3 and 4A, 4B and 4C should be employed.

These prior art figures, where the resilient means are indicated by the same reference numbers, show that rolls 40 and 42 are provided with jaw members 44 and 46, respectively. The jaw members 44 and 46 comprise non-resilient means 48 and 50, and resilient means 52 and 54, respectively. The rolls 40 and 42 are adjacent one another and have their axes parallel, being driven by any adequate conventional means.

When rotating, the rolls cooperate to engage the jaw members so that each non-resilient means compresses the opposite resilient means.

Figure 4:
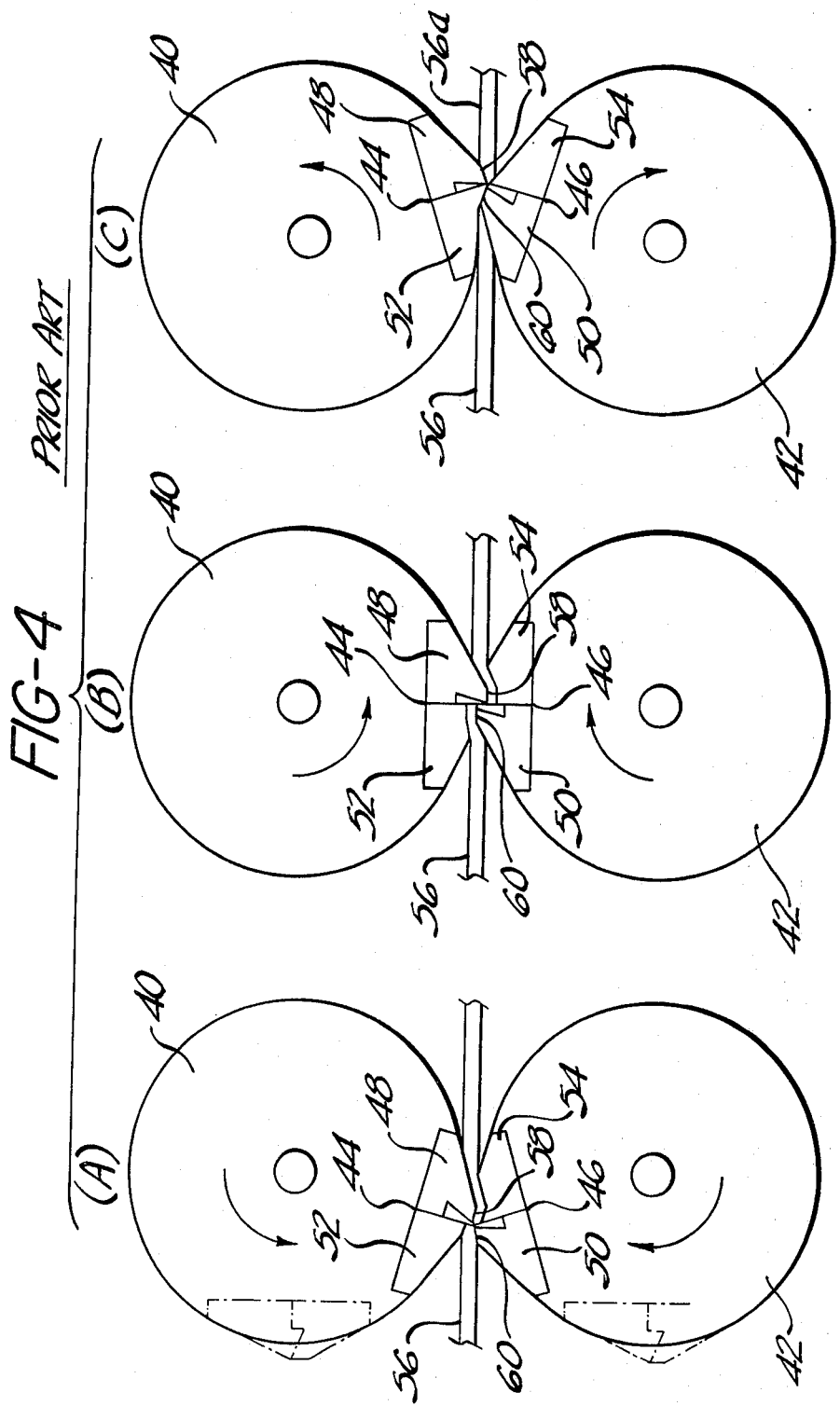
FIGS. 4A, 4B and 4C are schematic cross-sectional views of a prior art apparatus for the partitioning of panels.

As is more clearly shown in FIGS. 4A, 4B and 4C, the batt 56 of loosely compacted short fibers is conveyed in a path to a point of gripping 58 along a first transverse line with the resilient means 54 engaging a first surface of the batt 56 and non-resilient means 48 engaging the second surface of the batt. Immediately thereafter, the batt 56 is gripped along a second transverse line 60 adjacent the first transverse line 58 with a non-resilient means 50 engaging the first surface of the batt 56 and resilient means 50 engaging the second surface of the batt. In FIG. 4B the first and second lines 58 and 60 are displaced with respect to each other from the plane of the batt and on opposite sides of the plane. In FIG. 4C the batt is released to form and partition an individual panel 56A from the batt 56.

The transverse lines 58 and 60 lie immediately before and immediately after the point of partition of the fibrous batt 56.

Figure 3:
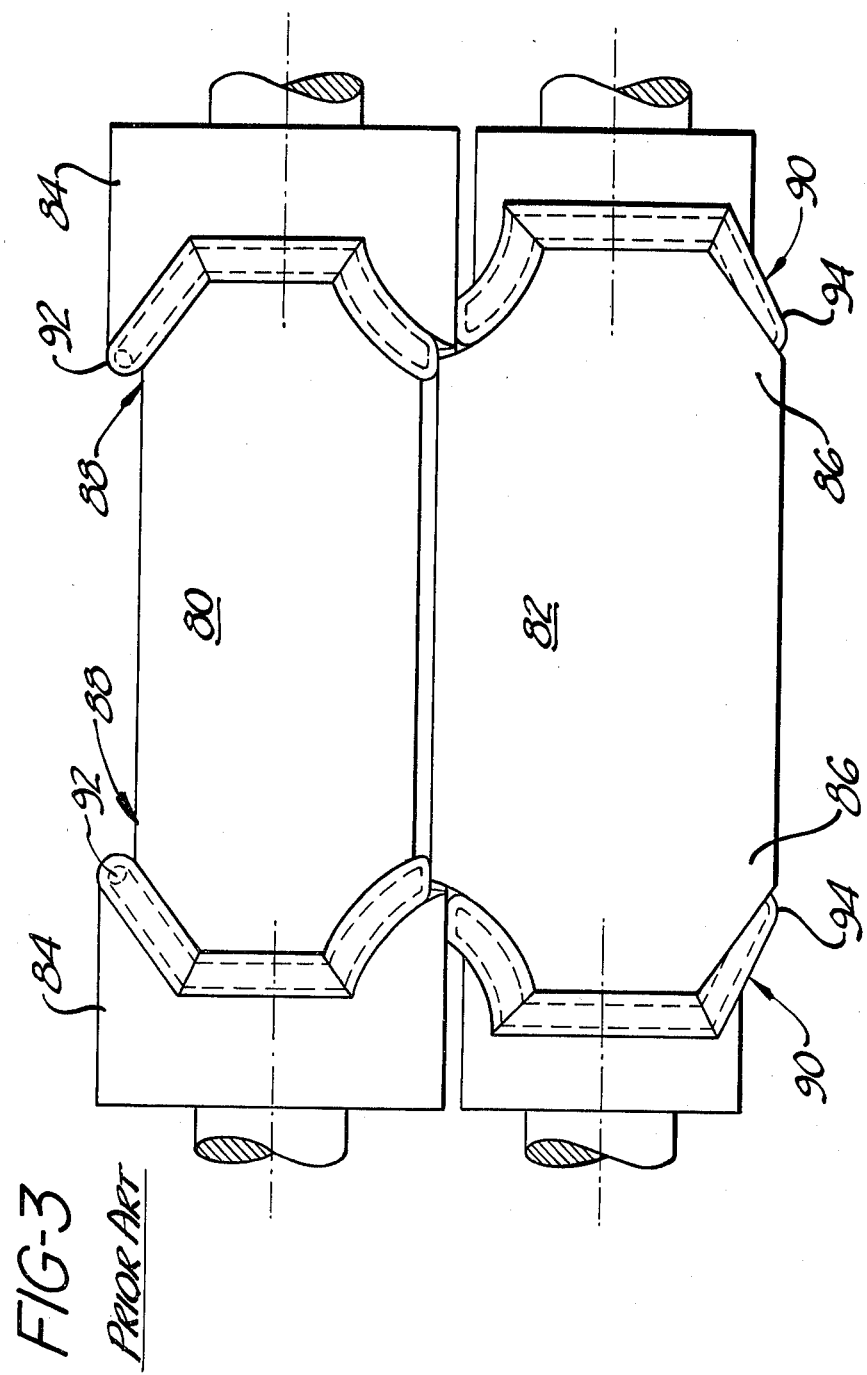
FIG. 3 is a front elevational view of a prior art apparatus for shaping panels.
Figure 5:
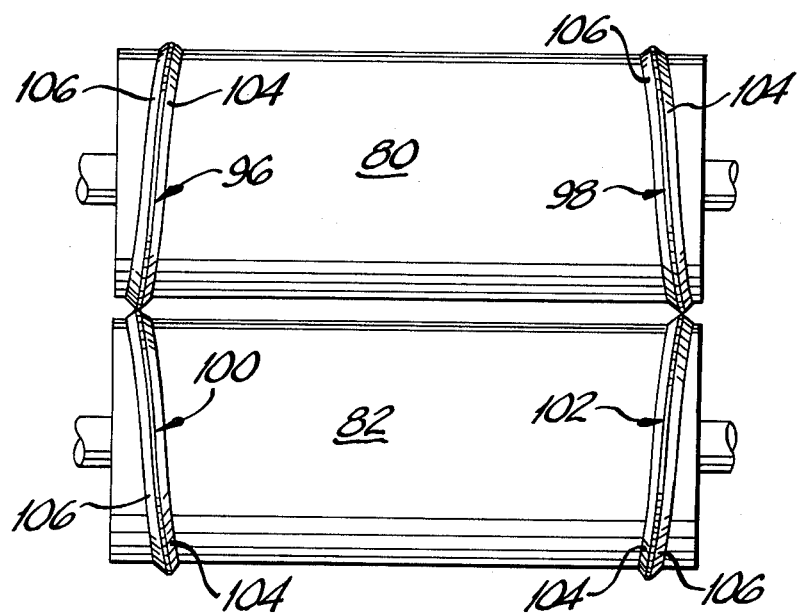
FIG. 5 is a front elevational view of a prior art apparatus for shaping panels.

Referring to FIGS. 3 and 5, there are shown other embodiments of apparatus in accordance with the present invention. In these embodiments, the apparatus is used to shape a batt of loose fibers. The apparatus comprises a pair of rolls 80 and 82 mounted for rotation in a frame not shown. The rolls are mounted adjacent one another with their axes parallel. The apparatus includes means (not shown) for rotating the rolls in opposite directions at the same peripheral linear speed.

As shown in FIG. 3, the rolls may be machined so as to have matching projections 84 and 86 and recesses 88 and 90 respectively along a portion of their peripheries in a pattern such as to produce the desired shape on the edges of the fibrous batt. In this embodiment, the projections 84 and 86 and the recesses 88 and 90 are non-resilient means of the roll. Held in the recessed portions 88 and 90 of each roll, adjacent to projecting portions 84 and 86 are respectively a resilient means 92 and 94. When rotating, the rolls cooperate to engage the projecting and recessed portions so that each non-resilient means compresses the opposite resilient means.

In FIG. 5 the rolls 80 and 82 are provided with jaw members 96, 98; 100 and 102, respectively. In this embodiment the jaw members 96, 98, 100 and 102 are mounted about the portion of the periphery of the rolls in a pattern so as to produce the desired shape in the batt. The jaw members comprise non-resilient means 104 and resilient means 106. When rotating, the rolls cooperate to engage the jaw members 96, 98, 100 and 102 so that each non-resilient means 104 compresses the opposite resilient means 106.

It should be made clear that various modifications and variations may be made to the present invention without departing from the spirit and scope of the claims attached. Thus, two resilient means may have several patterns with a cylindrical, rectangular, square or triangular cross-section, or have regular or irregular geometrical shapes, and may be hollow or, alternatively, contain closed or partially-closed cells. The resilient means may be held on the rolls by any conventional means, or may be placed on devices enabling their radial displacement or adjustment on the rolls. The resilient means may also have a surface cover of non-resilient material.

Such variations and modifications will depend, as may be easily seen by those skilled in the art, on the nature and the thickness of the fibrous batt to be partitioned and/or shaped. Thus, for example, the fibrous batt may in some cases have a surface skin.

Whether or not a skin is present, the partitioning and/or shaping afforded by the apparatus and method of the present invention eliminates formation of any densified layer or thickening at the edge of the panels.

We claim:

1. Method for partitioning a continuous batt of loosely compacted fibers into a plurality of individual panels, characterized by comprising: conveying the batt at a constant displacement speed in a certain direction; gripping the batt with two pairs of opposing resilient means arranged transversely relative to the direction of motion of the batt, and at a predetermined distance one pair from the other, said pairs of opposing resilient means consisting of a pair of trailing resilient means and a pair of leading resilient means; momentarily delaying the movement of the batt by an elastic reaction from the pair of trailing resilient means; momentarily advancing the batt, simultaneously to the momentary delay, by an elastic reaction of the pair of leading resilient means so as to stress the fibrous batt and sever it without the formation of compaction lines on the edges thus formed and without leaving the general plane of travel.

* * * * *